(12) United States Patent
Gibson

(10) Patent No.: US 11,337,389 B2
(45) Date of Patent: May 24, 2022

(54) LETTUCE VARIETY 'PRO 1339'

(71) Applicant: Progeny Advanced Genetics, Salinas, CA (US)

(72) Inventor: George Darryn Gibson, Prunedale, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/143,998

(22) Filed: Jan. 7, 2021

(65) Prior Publication Data

US 2021/0227767 A1   Jul. 29, 2021

Related U.S. Application Data

(60) Provisional application No. 62/965,356, filed on Jan. 24, 2020.

(51) Int. Cl.
*A01H 6/14* (2018.01)
*A01H 5/12* (2018.01)

(52) U.S. Cl.
CPC ............. *A01H 6/1472* (2018.05); *A01H 5/12* (2013.01)

(58) Field of Classification Search
None
See application file for complete search history.

(56) References Cited

U.S. PATENT DOCUMENTS 8,278,509 B2   10/2012   Gibson
9,832,967 B2 *  12/2017   Avila ................... A01H 6/1472

\* cited by examiner

*Primary Examiner* — Matthew R Keogh
*Assistant Examiner* — David R Byrnes
(74) *Attorney, Agent, or Firm* — Karen A. Magri

(57) ABSTRACT

A new lettuce variety designated 'PRO 1339' is described. 'PRO 1339' is a romaine lettuce variety exhibiting stability and uniformity.

9 Claims, No Drawings

LETTUCE VARIETY 'PRO 1339'

CROSS-REFERENCE TO RELATED APPLICATION

This application claims the benefit of U.S. Provisional Application No. 62/965,356, filed Jan. 24, 2020, which is hereby incorporated by reference in its entirety.

FIELD

This invention relates to the field of plant breeding. In particular, this invention relates to new lettuce, *Lactuca sativa*, variety, 'PRO 1339'.

BACKGROUND

Lettuce is an increasingly popular crop. Worldwide lettuce consumption continues to increase. As a result of this demand, there is a continued need for new lettuce varieties. In particular, there is a need for improved romaine lettuce varieties that exhibit improved growth habits, bolting and tip burn tolerance, and disease resistance.

SUMMARY

In order to meet these needs, the present invention is directed to an improved romaine lettuce variety with a light green color and early cupping growth habit that forms a dense heart, and has improved resistance to tip burn, as well as resistance to Tomato Bushy Stunt Virus (Tombusvirus), and corky root (*Rhizomonas suberifaciens*). In particular, the present invention is directed to lettuce, *Lactuca sativa*, seed designated as 'PRO 1339' having NCMA Accession Number 202202010. The present invention is further directed to a lettuce head isolated from a *Lactuca sativa* plant produced by growing 'PRO 1339' lettuce seed having NCMA Accession Number 202202010. The present invention is further directed to a *Lactuca sativa* plant having all the physiological and morphological characteristics of a *Lactuca sativa* plant produced by growing 'PRO 1339' lettuce seed having NCMA Accession Number 202202010. The present invention is further directed to an $F_1$ hybrid *Lactuca sativa* plant having 'PRO 1339' as a parent, where 'PRO 1339' lettuce seed is grown from 'PRO 1339' seed having NCMA Accession Number 202202010.

The present invention is further directed to lettuce, *Lactuca sativa*, plants and lettuce heads isolated therefrom produced by growing 'PRO 1339' lettuce seed. The present invention is further directed to a *Lactuca sativa* plant and the lettuce head isolated therefrom having all the physiological and morphological characteristics of a *Lactuca sativa* plant produced by growing 'PRO 1339' lettuce seed having NCMA Accession Number 202202010. The present invention is further directed to an $F_1$ hybrid lettuce, *Lactuca sativa*, plant and a head isolated therefrom grown from the seed having 'PRO 1339' as a parent wherein 'PRO 1339' is grown from 'PRO 1339' lettuce seed having NCMA Accession Number 202202010.

The present invention is further directed to pollen isolated from 'PRO 1339' lettuce plants. The present invention is further directed to ovules isolated from 'PRO 1339' lettuce plants. The present invention is further directed to tissue culture of 'PRO 1339' lettuce plants.

The present invention is further directed to a method of selecting lettuce plants by: (a) growing more than one 'PRO 1339' lettuce plant, where the plants are grown from lettuce seed having NCMA Accession Number 202202010; and (b) selecting a plant from step (a). The present invention is further directed to lettuce plants and seeds produced therefrom, where the lettuce plants and seeds are isolated by the selection method of the invention.

The present invention is further directed to a method of breeding lettuce by crossing a lettuce plant with a plant grown from 'PRO 1339' lettuce seed having NCMA Accession Number 202202010. The present invention is further directed to lettuce plants, heads isolated therefrom, and seeds produced therefrom, where the lettuce plant is isolated by the breeding method of the invention.

DETAILED DESCRIPTION

Definitions

In order to more clearly understand the invention, the following definitions are provided:

Romaine Lettuce: Romaine lettuce is *Lactuca sativa* L. var. *longifolia* Lam; also known as Cos. The plant develops in an upright open or upright compact growing habit with coarse textured leaves. The leaves are longer than they are wide, cupping together to form an elongated loose head. Leaf margins are often entire or undulated, rarely frilled. Other leaves range in color from light green to dark green with a heavy midrib. Inner heart leaves are smaller and range from light yellow to light green in color.

Rogueing: Rogueing is the process in lettuce seed production where undesired plants are removed from a variety. The plants are removed because they differ physically from the general desired expressed characteristics of the variety. The differences can be related to size, color, maturity, leaf texture, leaf margins, growth habit, or any other characteristic that distinguishes the plant.

Market Stage: Market stage is the stage when a lettuce plant is ready for commercial lettuce harvest. In the case of a romaine lettuce variety, a romaine plant is at a marketable state when the heart has some density and the head has reached an adequate size and weight.

PIC Type: PIC is an acronym for Paris Island Cos, a specific type and characterization of romaine lettuce. A PIC type romaine refers to an often vigorous growing romaine type with a smooth leaf surface. PIC type romaine varieties are often less heat resistant and faster growing than Florida type romaines.

Florida Type: A Florida type romaine refers to a specific class of romaine varieties with improved heat and bolting resistance, a more savoyed leaf surface, and corky root resistance. This class of romaine is often less vigorous and slower growing than the PIC type.

Tip Burn: Tip burn is the marginal collapse and necrosis, at or near the leaf margin, of rapidly expanding inner leaves. The disorder generally occurs near harvest and can result in complete crop loss. Symptoms include vein discoloration and/or the development of brown to black spots at or near the leaf margin. These spots can be accompanied by the browning of the leaf veins in the affected area. Warm temperatures, excessive fertilization, an increase in light intensity and other factors that contribute to rapid plant growth can enhance the development of tip burn.

Tomato Bushy Stunt Virus (TBSV): Lettuce dieback was first observed in California in the mid-1980s, and reports of the disease have increased over the last 10 years. Complete crop losses have occurred in fields of romaine lettuce. Lettuce dieback is caused by several related Tombusviruses including TBSV and lettuce necrotic stunt virus (LNSV)

(Liu et al., 1999; Obermeier et al., 2001). These viruses are soilborne, highly stable, and mechanically transmitted, and have no confirmed vector organisms. The conditions affecting symptom development remain poorly understood. The disease is frequently observed in low-lying areas of fields with a prior history of flooding, suggesting that the virus may be carried in river water and/or that disease symptoms may be associated with increased root stresses such as those presented by excess moisture. No effective cultural or chemical control methods have yet been identified apart from avoiding fields with a history of TBSV or using long crop rotations.

"Resistance to Tomato Bushy Stunt," "resistance to Tomato Bushy Stunt Virus," or "resistance to TBSV" refers to a level of resistance in a lettuce variety as measured by visual symptoms when infected with the virus, and by marker analysis for the dominant Tvr1 gene. Resistance is deemed present when the variety is homozygous dominant for the Tvr1 gene, and then confirmed when symptoms are not present in at least 98% of a lettuce variety when exposed to TBSV.

Corky Root: The pathogen responsible for corky root is *Rhizomonas suberifaciens*. *R. suberifaciens*, is a soilborne gram-negative bacterium that is prevalent in most coastal lettuce growing areas but may not be present in inland regions. CA1 is the most common strain and is publically available from the ATCC (Accession Number 49355). Other useful strains include CA3 and CA15. Colonies of *R. suberifaciens* are initially translucent but later become opaque. The colonies are umbonate, compact colonies, which ultimately become wrinkled and have raised edges on S-medium as described in Van Bruggen, et al 1990, Host Range of *Rhizomonas suberifaciens*, the causal agent of corky root of lettuce. Plant Disease, 74:581-584. *R. suberifaciens* is an aerobic bacterium, ranging in morphology from small rods (0.6-1.4 μm by 0.3-0.6 μm) with one lateral flagellum to long filaments. The type strain CA1 and other equivalent strains of *R. suberifaciens* are publically available in the Salinas Valley of California growing in the soil of lettuce fields. These strains are quite common and can be isolated using any suitable method known in the art, and characterized strains are conveniently available from Dr. Ariena Van Bruggen at the University of California and Davis.

Corky root affects both leaf and head lettuce varieties. Disease symptoms are typically more severe when soil temperatures are warmer. Corky root is worse in fields where lettuce is grown consecutively. High soil nitrate levels can increase disease severity. Early symptoms of corky root are yellow bands on tap and lateral roots of lettuce seedlings. These yellow areas gradually expand, taking on a green-brown color and developing cracks and rough areas on the surface of the root. As disease severity increases, the entire taproot may become brown, severely cracked, and nonfunctional; the feeder root system will also be reduced and damaged. At this point, roots are very brittle and easily break off when examined. Corky root may cause internal discoloration of the root. When the root is severely diseased, aboveground symptoms consist of wilting during warm temperatures, stunting of plants, and generally poor and uneven growth. Corky root symptoms could be confused with ammonium toxicity, which causes a brick-red discoloration of the central portion of the root and wilting of lettuce foliage.

Taking into account these definitions, the present invention is directed to seeds of the lettuce variety 'PRO 1339', plants produced by growing 'PRO 1339' lettuce seeds, head isolated or harvested from the plants, one or more plants selected from a collection of 'PRO 1339' plants and seeds derived or produced there from; plants produced by crossing a lettuce plant with a 'PRO 1339' lettuce plant and seeds derived or produced there from.

Origin and Breeding History of the Variety 'PRO 1339'

'PRO 1339' is a tall and heavy PIC type romaine variety that forms dense heavy hearts and is adapted to the coastal production regions of California. This variety is distinct and unique to all other romaine lettuce varieties due to its combined disease and physiological resistances. 'PRO 1339' has a unique and valuable resistance package, as it is resistant to Tomato Bushy Stunt Virus and corky root, two very problematic diseases found throughout the Salinas valley of California. In addition to these disease resistances, 'PRO 1339' is also resistant to the physiological problems associated with internal tip burn, which is unique in a densely cupping romaine variety.

'PRO 1339' is a romaine lettuce variety developed from a hand pollinated cross of the Progeny Advanced Genetics proprietary breeding line 'B014' (unpatented) and the variety 'PRO 1497' (unpatented, breeder's designation '21.0031'). The two parental varieties were selected for their specific disease and physiological resistances, and their respective yield potential. A male sterile plant was selected from the 'B014' breeding population as the mother plant, guaranteeing that all seeds resulting form the cross were true F1s and not selfs.

'B014' is a tightly cupping and slow growing romaine variety with excellent densely formed heavy hearts and a low core. 'B014' is resistant to Tomato Bushy Stunt Virus, *Sclerotinia*, corky root, and tip burn, and possesses the MS7ms7 allele allowing it to segregate 50/50 for male sterility. 'B014' is, however, too small for current market demands.

'PRO 1497' (breeder's designation '21.0031'), the pollen-donating parent, is resistant to Tomato Bushy Stunt and *Bremia lactuca* races 16-33, but susceptible to corky root and tip burn. This variety was selected for its lighter green/yellow color, and its slow bolting tendencies.

The cross was made in Year 0, and through the single seed descent breeding method, we have developed a large and erect growing romaine variety with dense heavy hearts, and light green color well adapted to the coastal lettuce production regions of California. Through extensive field trialing and screenings, and marker analysis, 'PRO 1339' has demonstrated resistance to TBSV, corky root, and tip burn.

In Year 0, at our research facility in Watsonville, Calif., a cross was made on to a male sterile plant from the breeding line 'B014' with the breeding line '21.0031' (also known as 'PRO 1497') designated as the pollen donor. The F1 seed was harvested in the fall of Year 0 and designated as 'B014 X 21.0031'.

In May of Year 1, 20 F1 seeds of 'B014 X 21.0031' were planted in a green house facility in Watsonville, Calif., indicated by research line number PWAT119039. The non-sterile F1 plants were allowed to self-pollinate. The F2 seed was then harvested in bulk in October of Year 1. The seed was immediately cleaned, processed, blended, and prepared for planting.

One hundred and fifty random F2 seeds from line number PWAT119039 were planted in the same research facility and re-designated as PWAT129990. Segregation amongst the F2 population was noted and all plants were allowed to self pollinate and produce seed. The F3 seed from each plant was harvested and packaged individually in the spring of Year 2, 140 individual plants total. One seed from each package (plant) was removed and placed in one envelope and designated as PWAT1310791 and planted again in the same research facility in the spring of Year 3. The population was observed and segregation for phenotype and maturity was again evident and noted, and all plants were allowed to self-pollinate and produce seed. F4 seed from 128 individual plants was harvested, cleaned, and packaged individually in the fall of Year 3.

A single seed from each of the 128 F4 recombinant inbred lines (RILs) were planted in the spring of Year 4 in our San Joaquin valley research production field, designated as PSJV1410999. The plants were allowed to self-pollinate and 125 individual plants were harvested in the late summer.

This process was repeated in fall of Year 4, in a Yuma, Ariz. research production field, and a seed from each of the 125 F5 individual plants were planted, designated as PYM1411857. F6 seed from 120 of these individual plants was harvested in the spring of Year 5. This seed was immediately processed, and a seed from each of the 120 F6 plants was planted in our San Joaquin valley research production field that same spring, designated as PSJV1512577. This process was again repeated and the smaller and earlier bolting plants were removed, the remaining plants were allowed to self-pollinate and 69 F7 individual plants were harvested, designated PSJV1613556(1-69).

A trial was prepared containing each of the 69 F7 individual plants of the designated pedigree. The parent varieties, and susceptible and resistant standard varieties were also included in the trial as checks for the multiple diseases, adaptability and physiological defects. A research trial was planted in the Salinas valley in California in spring of Year 7 in a field known to be infected with TBSV. The trial was evaluated in summer of Year 7. All F7 lines were evaluated based on phenotypic uniformity, improved size, improved weight, and improved tolerances to tip burn and fringe burn when compared to the parent and check varieties. The F7 lines were also rated on their resistance to TBSV. After multiple evaluations of the trial, 23 F7 lines of this pedigree were selected as they out performed the parent varieties, their sibs, and the majority of other lines in the trial for the designated traits. PSJV1613556-64 was among the 23 F7 lines advanced.

Simultaneous to the trialing, 25 plants each of the 69 F7 individual plants were grown to seed in our San Joaquin valley research production field. These lines were rogued and allowed to self-pollinate and the F8 seed was harvested in bulk for each individual lines. Based on the trial data the 23 advanced F8 lines were processed and prepared for marker analysis and trialing. Marker analysis was conducted on the 23 lines to determine the resistance to Tomato Bushy Stunt Virus. Of the 23 lines, 11 were determined to be homozygous resistant to the virus, including PSJV1714956.

The 11 resistant F8 lines of this pedigree, along with their parent lines, and check varieties, were planted in multiple fields containing TBSV the following summer, in times and locations where tip burn pressure is high. The F8 lines were screened for resistance to the diseases present, as well as tip burn and fringe burn. Plant architecture, plant color and other important physiological traits were also noted. PSJV1714956 continued to be resistant to TBSV, while being free of the symptoms associated with tip and fringe burn. This line also rated higher than most of its sibs for the other physiological traits noted. Based on these results, the line was designated PX 1339 and was recommended for advancement.

1500 plants of PX 1339 were grown in a summer research seed production field where they were evaluated for uniformity at multiple stages of development and were noted to be uniform and stable. The F9 seed was harvested in bulk.

Large strip and plot trials were planted in the summer in the Salinas valley of California with multiple growers in multiple locations. The variety continued to perform for the desired traits and the decision was made to commercialize the variety, designated as 'PRO 1339'.

As evaluated in multiple seed production fields and commercial plantings for 2 generations (F8 and F9), 'PRO 1339' has been observed to be uniform and stable without variants. Variety Description Information As described in Table 1 and the Examples below, lettuce variety 'PRO 1339' has numerous distinguishing characteristics.

TABLE 1

| | |
|---|---|
| Plant Type: | Romaine |
| Seed: | |
| Seed Color: | Black |
| Light Dormancy: | No |
| Heat Dormancy: | Yes |
| Cotyledons: | |
| Shape of Cotyledons: | Spatulate |
| Shape of Fourth Leaf: | Elongated |
| Length/Width Index of Fourth Leaf: | 25 |
| Apical Margin: | Entire |
| Basal Margin: | Entire |
| Undulation: | Flat |
| Green Color: | Light green |
| Anthocyanin: | Absent |
| Distribution: | None |
| Rolling: | Absent |
| Cupping: | Slight |
| Reflexing: | None |
| Mature Leaves: | |
| Margin: | |
| Incision Depth (Deepest penetration of the margin): | Absent |
| Indentation (Finest Division of the Margin): | Entire |
| Undulation of the Apical Margin: | Absent |
| Green Color: | Light green |
| Anthocyanin | |
| Distribution: | None |
| Size: | Medium |
| Glossiness: | Glossy |
| Blistering: | Absent |
| Leaf Thickness: | Thick |
| Trichomes: | Absent |

Breeding and Selection

The present invention is further directed to the use of 'PRO 1339' lettuce in breeding and selection of new varieties.

A. Breeding

In lettuce breeding, lines are selected for certain desired appropriate characteristics. For example, one line may be selected for bolt tolerance in the fall growing conditions of the desert production locations of California and Arizona or for resistance to viruses such as TBSV, *Sclerotinia* or corky root (*Rhizomonas suberifaciens*). Another line may be selected for the size, color and texture of the lettuce head. Crosses are made, for example, to produce a medium to light green, tip burn resistant romaine lettuce with improved texture, and size for spring and summer harvest in the Salinas Valley of California.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is performed by procedures well known in the art of lettuce breeding.

The manual removal of anther tubes, though an effective means to ensure the removal of all self-pollinating possibilities, is very tedious and time consuming when a large number of crosses are to be made. The breeders have therefore adapted a well-documented and modified method of making crosses more efficiently using these methods. While typically crosses are made by first misting the designated male flowers to wash the pollen off prior to fertilization. This process of misting is a proven and effective means of pollen removal that assures crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later, the styles should spring back up and the two lobes of the stigma are visibly open in a "V" shape. Pollen from another variety or donor parent is then introduced by gently rubbing the stigma and style of the donor parent to the maternal parent. For this particular cross, the female plant is genetically male sterile and therefore does not produce pollen. Crossing on to male sterile flowers is a more effective way to eliminate selfing and guarantee all resultant seeds are truly F1's. Tags with the pertinent information on date and pedigree are then secured to the female flowers in order to keep track of the cross.

About 3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the F2 generations when expected segregation patterns for the genetic character of interest can be followed. This latter situation mandates a lengthy wait to determine if hybrids are produced. Two relevant references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908 both of which are hereby incorporated by reference in their entirety for the purpose of providing details on the techniques well known in the art.

B. Selection

In addition to crossing, selection may be used to identify and isolate new lettuce lines. In lettuce selection, lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determine if they exhibit the desired characteristics of the originally selected line. Selection work is continued over multiple generations to increase the uniformity of the new line.

DEPOSIT INFORMATION

A deposit of the lettuce variety 'PRO 1339' is maintained by Progeny Advanced Genetics, having an address at 590A Works Street, Salinas, Calif. 93901, United States of America. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the Provasoli-Guillard National Center for Marine Algae and Microbiota (NCMA) at Bigelow Laboratory for Ocean Sciences, 60 Bigelow Drive, East Boothbay, Me., 04544 U.S.A.

Applicants have made available to the public without restriction a deposit of at least 625 seeds of lettuce variety 'PRO 1339' with the Provasoli-Guillard National Center for Marine Algae and Microbiota (NCMA) at Bigelow Laboratory for Ocean Sciences, 60 Bigelow Drive, East Boothbay, Me., 04544 U.S.A. with a deposit on Feb. 22, 2022 which has been assigned NCMA number 202202010.

The deposit will be maintained in the NCMA depository, which is a public depository, for a period of 30 years, or 5 years after the most recent request, or for the effective life of the patent, whichever is longer, and will be replaced if a deposit becomes nonviable during that period.

This invention will be better understood by reference to the following non-limiting Examples.

Examples

Example 1: General Trialing Method

The following steps illustrate the general trialing method of the invention:

I. Set Up
1. A trial is set up to compare one or more lines. Parental lines and related varieties are identified.
2. Primary slots are identified.
3. Accession lines are located and purchased/obtained from seed dealers or growers.
4. All varieties are assigned a number to maintain integrity and anonymity.
5. Trials are set up in with all necessary varieties. Variety arrangement for trial is diagramed.

II. Planting
1. Commercial plantings are located by contacting commercial growers during the planting slot recommended for the variety.
2. A field is located during commercial planting and the necessary rows and area is marked off.
3. Varieties are planted according to a diagram, generally in 100 foot ranges.
4. All varieties are planted in same manner to mimic the planting of the commercial variety as closely as possible.
5. A trial map is drawn diagramming the trial, the trial location in the field and directions to the field.

III. Maintenance
1. All varieties are treated identically. Plants are watered, fertilized, and treated to control pests in the same manner as other lettuce plants in the commercial field.
2. The trial is thinned to separate the plants for optimum growth.

IV. Evaluation
1. Evaluations are done as near to the time of the commercial harvest as possible.
2. The evaluation is conducted "blindly". That is, the evaluator(s) do not have the key to the trial at the time of evaluation.

3. 30 heads of each variety are evaluated.
   a. The frame diameters of 30 random plants are measured to the nearest cm.
   b. 30 mature heads of each variety are cut to the cap leaf.
   c. The heads are carried to an adequate work station
   d. The following measurements are often then conducted and recorded:
      1. Each head is weighed to the nearest gram.
      2. The core diameter of each head is measured to the nearest mm.
      3. The heads are then sliced in to halves, discarding 1 half
      4. The core lengths (from the cut stem to the core tip) are measured to the nearest mm.
      5. The plant length (from the cut stem to the cap leaf) is measured to the nearest mm.
      6. The plant diameter (at its widest point) is measured to the nearest mm.
      7. The heart length is measured to the nearest mm.
      8. The ideal maturity or harvest date is then estimated based on the solidity of the head, the core length and any other physiological characteristics present.
      9. The leaf color is documented using the Munsell Color Charts for Plant Tissue.
   e. From these measurements, an Excel program is used to calculate the averages, the standard deviations and the T-Tests for the compared varieties.

Example 2: Comparative Analysis

Following the procedures of Example 1, 'PRO 1339' romaine lettuce was compared to various other varieties. Comparative data was obtained and analyzed for different romaine lettuce lines to determine their comparative resistance to Tomato Bushy Stunt Virus, corky root resistance, and tip burn resistance.

'PRO 1339' is a unique and distinct romaine lettuce variety with a light green color and densely cupping growth habit compared to similar varieties. 'PRO 1339' has a slow to medium growing growth habit, and forms very dense and heavy hearts.

The most distinguishing characteristics of 'PRO 1339' are the unique multiple resistances and improved adaptability to multiple end uses. 'PRO 1339' is resistant to the Tombusvirus known as Tomato Bushy Stunt Virus (TBSV) and corky root (*Rhizomonas suberifaciens*). 'PRO 1339' is also highly resistant to tip burn. Its dense heavy hearts, and narrow upright growth make it very suitable and desirable for the processing and romaine hearts market.

Resistance to corky root is determined by PCR marker analysis. PCR marker analysis was done to determine the presence of the recessive 'cor' gene. 10 plants of each test line were screened with the marker. Table 2 shows that based on PCR analysis for 'cor', the varieties 'PRO 1339' and 'B014' are homozygous recessive for the 'cor' gene, making the varieties resistant to corky root. 'PRO 1497' is homozygous dominant for 'cor', making it susceptible to the disease.

TABLE 2

| Plant No. | Corky Root Resistance based PCR analysis of individual plants | | |
|---|---|---|---|
| | PRO 1339 | PRO 1497 | B014 |
| 1 | Resistant | Susceptible | Resistant |
| 2 | Resistant | Susceptible | Resistant |

TABLE 2-continued

| Plant No. | Corky Root Resistance based PCR analysis of individual plants | | |
|---|---|---|---|
| | PRO 1339 | PRO 1497 | B014 |
| 3 | Resistant | Susceptible | Resistant |
| 4 | Resistant | Susceptible | Resistant |
| 5 | Resistant | Susceptible | Resistant |
| 6 | Resistant | Susceptible | Resistant |
| 7 | Resistant | Susceptible | Resistant |
| 8 | Resistant | Susceptible | Resistant |
| 9 | Resistant | Susceptible | Resistant |
| 10 | Resistant | Susceptible | Resistant |

Resistance to Tomato Bushy Stunt Virus (TBSV) was determined first by marker analysis for the Tvr1 gene. Plants were deemed resistant when the marker data showed to be homozygous dominant for this gene. Table 3 shows that based on PCR analysis for Tvr1 gene, the varieties 'PRO 1339', 'PRO 1497', and 'B014' are homozygous dominant for the Tvr1 gene, making the varieties resistant to TBSV.

TABLE 3

Results of PCR Analysis to Determine Tomato Bushy Stunt Resistance

| Plant No. | Tomato Bushy Stunt Resistance based PCR analysis of individual plants | | |
|---|---|---|---|
| | PRO 1339 | PRO 1497 | B014 |
| 1 | Resistant | Resistant | Resistant |
| 2 | Resistant | Resistant | Resistant |
| 3 | Resistant | Resistant | Resistant |
| 4 | Resistant | Resistant | Resistant |
| 5 | Resistant | Resistant | Resistant |
| 6 | Resistant | Resistant | Resistant |
| 7 | Resistant | Resistant | Resistant |
| 8 | Resistant | Resistant | Resistant |
| 9 | Resistant | Resistant | Resistant |
| 10 | Resistant | Resistant | Resistant |

The resistance to TBSV was then confirmed by growing the test variety 'PRO 1339' against known susceptible variety 'Solid King' (U.S. Pat. No. 8,524,981) in fields where TBSV was present. The test plots were made as equivalent as possible using standard field plotting techniques and resistance was defined by visible infection. Infected plants can be severely stunted when mature, diseased plants may only reach 6 to 8 inches in height. The outermost leaves are extensively yellowed. The younger, inner leaves often remain dark green in color, but can be rough and leathery in texture. In some cases, the older leaves develop necrotic spotting that can turn into extensive areas of brown, dead tissue. There is no partial infection to provide relative scoring. The plants are either infected and scored with a '1' and die, or not infected and scored with a '0'. Table 4 below shows results and statistical analysis of three trials that compare TBSV resistance of 30 plants of the lettuce variety 'PRO 1339' with that of 30 plants of lettuce variety 'Solid King'. The first and second trials were performed in Soledad, Calif. and the third trial was performed in Salinas, Calif. The results clearly show that 'PRO 1339' is resistant to TBSV (data all statistically significant at a minimum of 95% confidence level).

TABLE 4

| | Mortality from TBSV | | | | | |
| --- | --- | --- | --- | --- | --- | --- |
| | Trial 1 | | Trial 2 | | Trial 3 | |
| Plant | PRO 1339 | Solid King | PRO 1339 | Solid King | PRO 1339 | Solid King |
| 1 | 0 | 1 | 0 | 1 | 0 | 0 |
| 2 | 0 | 1 | 0 | 0 | 0 | 0 |
| 3 | 0 | 1 | 0 | 0 | 0 | 0 |
| 4 | 0 | 1 | 0 | 0 | 0 | 1 |
| 5 | 0 | 0 | 0 | 0 | 0 | 0 |
| 6 | 0 | 1 | 0 | 1 | 0 | 0 |
| 7 | 0 | 1 | 0 | 1 | 0 | 0 |
| 8 | 0 | 1 | 0 | 1 | 0 | 1 |
| 9 | 0 | 0 | 0 | 1 | 0 | 1 |
| 10 | 0 | 0 | 0 | 0 | 0 | 1 |
| 11 | 0 | 0 | 0 | 0 | 0 | 1 |
| 12 | 0 | 0 | 0 | 1 | 0 | 0 |
| 13 | 0 | 0 | 0 | 0 | 0 | 0 |
| 14 | 0 | 0 | 0 | 1 | 0 | 0 |
| 15 | 0 | 0 | 0 | 0 | 0 | 0 |
| 16 | 0 | 1 | 0 | 1 | 0 | 1 |
| 17 | 0 | 1 | 0 | 0 | 0 | 1 |
| 18 | 0 | 1 | 0 | 0 | 0 | 1 |
| 19 | 0 | 0 | 0 | 0 | 0 | 1 |
| 20 | 0 | 1 | 0 | 0 | 0 | 1 |
| 21 | 0 | 0 | 0 | 0 | 0 | 0 |
| 22 | 0 | 1 | 0 | 1 | 0 | 1 |
| 23 | 0 | 0 | 0 | 1 | 0 | 0 |
| 24 | 0 | 0 | 0 | 1 | 0 | 1 |
| 25 | 0 | 1 | 0 | 1 | 0 | 0 |
| 26 | 0 | 1 | 0 | 1 | 0 | 1 |
| 27 | 0 | 1 | 0 | 0 | 0 | 0 |
| 28 | 0 | 0 | 0 | 1 | 0 | 0 |
| 29 | 0 | 0 | 0 | 0 | 0 | 0 |
| 30 | 0 | 1 | 0 | 1 | 0 | 0 |
| Average | 0 | 0.533333333 | 0 | 0.5 | 0 | 0.433333333 |
| Standard Deviation | 0 | 0.507416263 | 0 | 0.508547628 | 0 | 0.504006933 |
| t-test | 3.41662E−07 | | 1.37026E−06 | | 1.59302E−05 | |
| Probability | 100.00 | | 100.00 | | 100.00 | |
| % Mortality | 0.0 | 53.3 | 0.0 | 50.0 | 0.0 | 43.3 |

Resistance to tip burn was determined by growing the test variety, 'PRO 1339' against a known susceptible variety, 'PRO 1497' (unpatented) in conditions, locations and time periods where tip burn was an issue. The test plots were made as equivalent as possible using standard field plotting techniques and resistance was defined by lack of visible defects. Plants are cut, and the internal leaves are exposed and inspected for symptoms of tip burn. Plants observed with symptoms of tip burn are scored with a '1', and plants with no symptoms are scored with a '0'. Table 5 below shows results and statistical analysis of three trials that compare TBSV resistance of 30 plants of the lettuce variety 'PRO 1339' with that of 30 plants of lettuce variety 'PRO 1497'. The first and second trials were performed in Soledad, Calif. and the third trial was performed in Salinas, Calif. The results clearly show that 'PRO 1339' is resistant to tip burn (data all statistically significant at a minimum of 95% confidence level).

TABLE 7

| | Tip burn presence | | | | | |
| --- | --- | --- | --- | --- | --- | --- |
| | Trial 1 | | Trial 2 | | Trial 3 | |
| Plant | PRO 1339 | PRO 1497 | PRO 1339 | PRO 1497 | PRO 1339 | PRO 1497 |
| 1 | 0 | 0 | 0 | 1 | 0 | 0 |
| 2 | 0 | 0 | 0 | 1 | 0 | 0 |
| 3 | 0 | 0 | 0 | 0 | 0 | 0 |
| 4 | 0 | 0 | 0 | 0 | 0 | 1 |
| 5 | 0 | 1 | 0 | 0 | 0 | 1 |
| 6 | 0 | 1 | 0 | 1 | 0 | 1 |
| 7 | 0 | 1 | 0 | 1 | 0 | 0 |
| 8 | 0 | 0 | 0 | 1 | 0 | 0 |
| 9 | 0 | 0 | 0 | 1 | 0 | 1 |
| 10 | 0 | 0 | 0 | 1 | 0 | 0 |
| 11 | 0 | 1 | 0 | 0 | 0 | 1 |
| 12 | 0 | 0 | 0 | 0 | 0 | 0 |
| 13 | 0 | 0 | 0 | 0 | 0 | 1 |
| 14 | 0 | 0 | 0 | 0 | 0 | 0 |
| 15 | 0 | 1 | 0 | 0 | 0 | 0 |

TABLE 7-continued

| | Tip burn presence | | | | | |
| | Trial 1 | | Trial 2 | | Trial 3 | |
| Plant | PRO 1339 | PRO 1497 | PRO 1339 | PRO 1497 | PRO 1339 | PRO 1497 |
|---|---|---|---|---|---|---|
| 16 | 0 | 0 | 0 | 0 | 0 | 0 |
| 17 | 0 | 1 | 0 | 1 | 0 | 1 |
| 18 | 0 | 0 | 0 | 0 | 0 | 1 |
| 19 | 0 | 1 | 0 | 1 | 0 | 0 |
| 20 | 0 | 0 | 0 | 0 | 0 | 0 |
| 21 | 0 | 0 | 0 | 0 | 0 | 0 |
| 22 | 0 | 0 | 0 | 0 | 0 | 0 |
| 23 | 0 | 0 | 0 | 1 | 0 | 1 |
| 24 | 0 | 1 | 0 | 1 | 0 | 1 |
| 25 | 0 | 0 | 0 | 1 | 0 | 0 |
| 26 | 0 | 0 | 0 | 0 | 0 | 1 |
| 27 | 0 | 1 | 0 | 0 | 0 | 0 |
| 28 | 0 | 0 | 0 | 0 | 0 | 1 |
| 29 | 0 | 1 | 0 | 1 | 0 | 0 |
| 30 | 0 | 1 | 0 | 1 | 0 | 0 |
| Average | 0.00 | 0.37 | 0.00 | 0.47 | 0.00 | 0.40 |
| Standard Deviation | 0.00 | 0.49 | 0.00 | 0.51 | 0.00E+00 | 4.98E−01 |
| t-test Probability | 0.000131392 | | 4.91E−06 | | 4.75E−05 | |
| % Difference | 99.99 100.0 | | 100.00 100.0 | | 100.00 100.0 | |
| Confidence Interval | 0.041 | 0.087 | 0.054 | 0.063 | 0.042 | 0.081 |

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed:

1. A Lactuca sativa seed designated as 'PRO 1339' having NCMA Accession Number 202202010.

2. A Lactuca sativa plant produced by growing the seed of claim 1.

3. A lettuce head isolated from the plant of claim 2.

4. A Lactuca sativa plant having all the physiological and morphological characteristics of the Lactuca sativa plant of claim 2.

5. An F1 hybrid Lactuca sativa plant having 'PRO 1339' as a parent where 'PRO 1339' is grown from the seed of claim 1.

6. Pollen of the plant of claim 2.

7. An ovule of the plant of claim 2.

8. A tissue culture of the plant of claim 2.

9. A method of selecting a lettuce plant, comprising:
   a) growing a plurality of plants from a plurality of the seed of claim 1; and
   b) selecting a plant from the plurality of plants of step a).

* * * * *